United States Patent
Gillies et al.

(10) Patent No.: US 9,438,869 B2
(45) Date of Patent: Sep. 6, 2016

(54) IMAGE PROJECTOR SYSTEM FOR A SCANNING ROOM

(75) Inventors: Murray Fulton Gillies, Eindhoven (NL); Wilhelmus Daniel Hyacintus Van Groningen, Eindhoven (NL); Gijs Antonius Franciscus Van Elswijk, Eindhoven (NL); Jurgen Vogt, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 453 days.

(21) Appl. No.: 13/883,781

(22) PCT Filed: Oct. 17, 2011

(86) PCT No.: PCT/IB2011/054590
§ 371 (c)(1),
(2), (4) Date: May 7, 2013

(87) PCT Pub. No.: WO2012/066434
PCT Pub. Date: May 24, 2012

(65) Prior Publication Data
US 2013/0235168 A1    Sep. 12, 2013

(30) Foreign Application Priority Data

Nov. 17, 2010 (EP) .................................. 10191505

(51) Int. Cl.
| | |
|---|---|
| *H04N 9/31* | (2006.01) |
| *A61B 5/055* | (2006.01) |
| *A61B 5/00* | (2006.01) |
| *G01R 33/28* | (2006.01) |

(52) U.S. Cl.
CPC ............... *H04N 9/31* (2013.01); *A61B 5/0046* (2013.01); *A61B 5/055* (2013.01); *A61B 5/742* (2013.01); *G01R 33/28* (2013.01); *G01R 33/288* (2013.01)

(58) Field of Classification Search
CPC ........................................................ H04N 9/31
USPC ............................................... 348/51, 53, 54
See application file for complete search history.

(56) References Cited

U.S. PATENT DOCUMENTS

| | | | |
|---|---|---|---|
| 4,804,261 A | 2/1989 | Kirschen | |
| 5,076,275 A | 12/1991 | Bechor et al. | |
| 5,414,459 A | 5/1995 | Bullwinkel | |
| 5,864,331 A * | 1/1999 | Anand et al. | 345/656 |
| 6,431,711 B1 * | 8/2002 | Pinhanez | 353/69 |
| 6,774,929 B1 | 8/2004 | Kopp | |
| 6,959,266 B1 | 10/2005 | Mostafavi | |

(Continued)

FOREIGN PATENT DOCUMENTS

| | | |
|---|---|---|
| DE | 10156818 | 5/2003 |
| JP | 2005192908 A | 7/2005 |

(Continued)

*Primary Examiner* — Paulos M Natnael

(57) ABSTRACT

The invention relates to a method and a system for reducing anxiety of patients before and during e.g. MR scanning examinations. The method is based on displaying images on walls (106,107) of the scanner room (100) so that when the patient enters the scanner room, then an image is displayed on a wall visible to the patient, e.g. a wall adjacent to the entry door (103). When the patient is laying on the table (102) of the scanner (101) the projection of images is switched to another wall by reflecting the projected images using e.g. a mirror which is moved into the light rays emitted by an image projector.

10 Claims, 3 Drawing Sheets

(56) References Cited

U.S. PATENT DOCUMENTS

| | | |
|---|---|---|
| 7,030,615 B2 | 4/2006 | Gortler |
| 7,702,375 B2 | 4/2010 | Boninger et al. |
| 8,363,861 B2* | 1/2013 | Hughes et al. ............... 381/189 |
| 2002/0105623 A1 | 8/2002 | Pinhanez |
| 2005/0007514 A1 | 1/2005 | Faris et al. |
| 2005/0128437 A1 | 6/2005 | Pingali et al. |
| 2005/0283068 A1 | 12/2005 | Zuccolotto et al. |
| 2006/0209257 A1* | 9/2006 | Bullwinkel ................... 351/210 |
| 2007/0097320 A1 | 5/2007 | Ullmann |
| 2009/0154647 A1* | 6/2009 | Matsuzawa et al. ........... 378/98 |
| 2011/0080335 A1* | 4/2011 | Unger et al. .................. 345/156 |

FOREIGN PATENT DOCUMENTS

| | | |
|---|---|---|
| JP | 2007086545 A | 9/2005 |
| JP | 2006288908 A | 10/2006 |
| JP | 2007279339 A | 10/2007 |
| WO | WO2005120341 | 12/2005 |
| WO | WO2010105153 | 9/2010 |

* cited by examiner

IMAGE PROJECTOR SYSTEM FOR A SCANNING ROOM

FIELD OF THE INVENTION

The invention relates to systems and methods for reducing anxiety of patients, in particular to systems suited for use in scanner rooms.

BACKGROUND OF THE INVENTION

Patients that undergo scanning examinations, for example MR scans, are often highly stressed. The long and narrow tunnel of MR scanners creates a feeling of confinement and, therefore, increases anxiety or induces claustrophobia type symptoms.

The quality of scanning results may be negatively affected if a patient is highly anxious. Therefore, in order to improve scanning results or at least for improving the comfort of patients there is a need for reducing or compensating patient's negative experience of scanners and scanner rooms.

U.S. Pat. No. 6,774,929 discloses an MR video system that provides visual stimuli to a patient who is undergoing diagnostic treatment within a magnetic resonance imagery (MR) apparatus. The system utilizes a magnetically inert and RF shielded projector located in the close proximity to the MR apparatus to transpose a video picture on a translucent screen inside the bore of the MR apparatus. The patient views the screen through a prism.

Whereas U.S. Pat. No. 6,774,929 discloses a system which may improve the comfort of patients in scanner rooms, the inventor of the present invention has appreciated that improvements for improving patient comfort are needed, and has in consequence devised the present invention.

SUMMARY OF THE INVENTION

It would be advantageous to achieve improvements for reducing anxiety of patients both before and during scanning examinations. In particular, it may be seen as an object of the present invention to provide a method that solves the above mentioned problems caused by scanners, or other problems, of the prior art.

To better address one or more of these concerns, in a first aspect of the invention an image projection system for use in a scanner room for patient examination is presented where an image projector is installed in the scanner room for projecting an image onto a surface of the room, the image projection system comprises a reflector unit comprising a reflector, where the reflector is positioned relative to the image projector so that in a first mode of the reflector unit the image is projected onto a first room surface, and in a second mode of the reflector unit the image is projected onto a second room surface, where the first and second room surfaces are non-coincident, and where a change from the first to the second mode is dependent on an input signal, a signal generator for generating the input signal indicative of a location of the patient.

The reflector unit may comprise an input for receiving the input signal from the signal generator.

Non-coincident first and second surfaces may be first and second areas on a wall which are distanced relative to each other, the first and second surfaces may be two walls of a room, e.g. non-parallel or parallel walls. Any of the first and second surfaces may comprise different or non-coincident areas of walls, the floor or the ceiling of the room. A room surface may also be a surface of a scanner located in the room.

The reflector unit may be a separate component designed to be placed near the image projector, or the reflector unit may be a component of the image projector. However, advantageously the reflector unit is a separate component which may be used with any image projector. Since the image from the same projector can be projected onto different surfaces of the scanner room, the patient is able to see projected image even when the patient takes different positions within the scanner room.

In an embodiment the image projection system further comprises a viewing device with one or two reflectors arranged to change the viewing path from a path between the patient and the first room surface to a path between the patient and the second room surface.

Thus, the one or two reflectors may be arranged to change the optical path from patient to the projected image such that the patient can see the projected image when the reflector unit is in the second mode. In other words, the viewing direction of a patient may be redirected by the one or two reflectors to enable the patient to see the projected image when the reflector unit is in the second mode.

In an embodiment the first surface is a surface adjacent to a patient entry of the scanner room and the second surface is a surface visible to a patient lying on a table of a scanner of the scanner room.

In an embodiment the signal generator is a manually operable switch. E.g. the switch may be operable by the patient or clinical personnel. Accordingly, the patient is able to determine when he wishes to see the image after he is lying on the scanner table.

In another embodiment the signal generator is a detector capable of detecting when the patient is in a particular position required for performing a scanning operation. Accordingly, the patient need not consider or take any actions for causing images to be visible when he is lying on the scanner table.

In an embodiment the image projector is switchable between projecting 2D images and 3D images so that 2D images are projected when the reflector unit is in the first mode and 3D images are projected when the reflector is in the second mode, where projection of 3D images comprises projection of mutually displaced first and second images which are coded, such as color or polarization coded, so that the first and second images are viewable by the respective left and right eye of the patient. Advantageously, 3D images may enhance the viewing experience so that the anxiety of a patient may be reduced more in comparison with 2D images.

In an embodiment the viewing device comprises coded viewing elements, such as color or polarization coded, for the respective left and right eye of the patient to enable viewing of the respective first and second images according to the embodiment of displaying 3D images.

In an embodiment the image projector is configured to generate a border around the image. The appearance of the border may be set in correspondence of the appearance of the room lighting. When the border corresponds to the field of view enabled by the viewing device or the tunnel of the scanner, the viewing experience may not be negatively affected due to the reduced field of view since the border may create an impression that the field of view is not limited.

In an embodiment the reflector unit is further switchable into a third mode where the image is projected onto a third surface which provides the patient entry to the scanner room. Therefore, when the patient leaves the scanner room he is presented with the image. This may be advantageous, since the final impression of the scan room will often determine the memory of the experience. For maximum patient comfort it is therefore important that the last viewed surface of the MR room is also part of the personally chosen room theme.

An embodiment of the image projection system comprises a patient monitoring unit for detecting physiological parameters of the patient where the control unit has a processor for generating or modifying the image signal containing image information supplied to the image projector. Accordingly, the projected images may be set in dependence of the physiological parameters. Furthermore, if the heart rate increases calming music may be played.

In an embodiment the image projection system according to claim comprises a surveillance system with a camera, where the system has image processing capabilities for detecting the presence of clinical personnel, and in dependence of a detected presence of clinical personnel changing a condition of the scanner room, such as the lighting intensity.

A second aspect of the invention relates to a method for improving patient comfort in a scanner room for patient examination by projecting images onto a room surface by use of an image projector installed in the scanner room, where the method comprises generating a signal indicating a location of a patient within the scanner room, in dependence of the location given by the generated signal, projecting an image from the image projector onto a first surface if the signal indicates a first location and, projecting the image from the same image projector onto a second surface by redirecting the image using a reflector unit if the signal indicates a second location different from the first location, where the first and second room surfaces are non-coincident.

In general the various aspects of the invention may be combined and coupled in any way possible within the scope of the invention. These and other aspects, features and/or advantages of the invention will be apparent from and elucidated with reference to the embodiments described hereinafter.

In summary the invention relates to a method and a system for reducing anxiety of patients before and during e.g. MR scanning examinations. The method is based on displaying images on walls of the scanner room so that when the patient enters the scanner room, then an image is displayed on a wall visible to the patient, e.g. a wall adjacent to the entry door. When the patient is laying on the table of the scanner the projection of images is switched to another wall by reflecting the projected images using e.g. a mirror which is moved into the light rays emitted by an image projector.

BRIEF DESCRIPTION OF THE DRAWINGS

Embodiments of the invention will be described, by way of example only, with reference to the drawings, in which.

DESCRIPTION OF EMBODIMENTS

Figure 1:
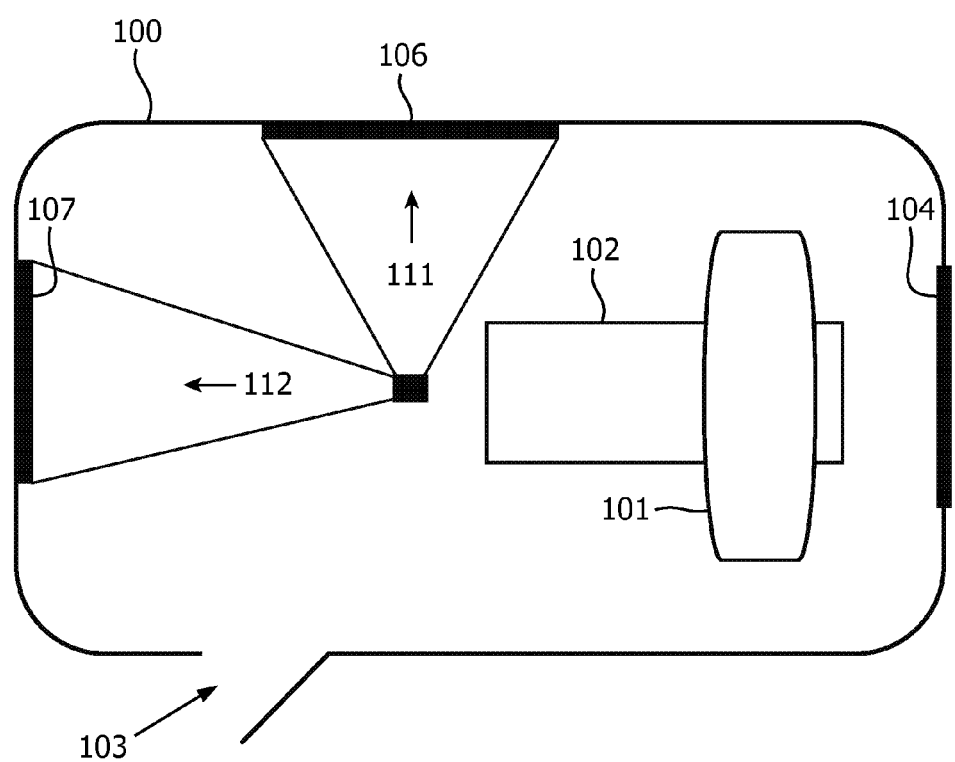
FIG. 1 shows a scanner room with a scanner.

FIG. 1 shows a scanner room 100 with a scanner 101 such as an MR-scanner for scanning a patient (not shown) lying on the table 102. The scanner room 100 has a patient entry 103 such as a door and window 104 which allows clinic personnel located outside the scanning room to watch the patient during the scanning process.

An image projector 105 is installed in the scanner room for projecting an image onto a surface 106 of the room. The projected image content may be a still image or video images supplied to the image projector 105 as image data, e.g. from a computer.

A reflector unit (202, see FIG. 2) is arranged in relation to the image projector 105 for redirecting the projected image into a first direction 112 different than the projection direction 111 of the image projector. Possibly, the image may be redirected into further directions different than the projection direction and the first direction.

For example, the reflector unit 202 may be switchable into a third mode where the image is projected onto a wall surface which provides the patient entry 103 to the scanner room.

Thus, in a first mode of the reflector unit the image is projected along the projection direction 111 onto a first room surface, e.g. surface 106 and in a second mode of the reflector the image is projected along the first direction 112 onto a second room surface.

The first and second surfaces 106 and 107 may be walls of the room, the ceiling or floor of the room, or even the scanner itself where the projected image camouflages the presence of the scanner itself. The first and second surfaces 106 and 107 are different surfaces of the room, i.e. the first and second room surfaces are non-coincident, e.g. non-parallel or perpendicular, with respect to each other.

Figure 2:
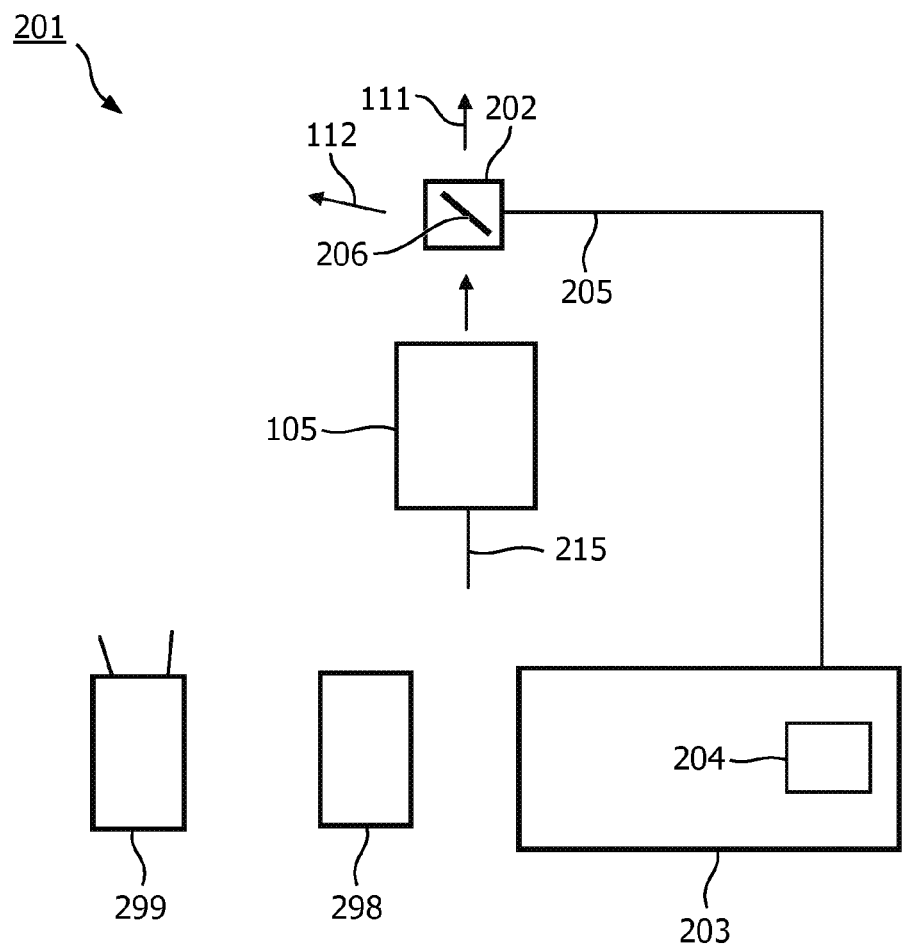
FIG. 2 shows an image projection system with a reflector unit.

FIG. 2 shows an image projection system 201 which comprises the reflector unit 202 and a control unit 203 connectable with an input 205 of the reflector unit 202 The input 205 is intended for receiving an input signal for controlling the actual mode of the reflector unit.

The input signal may be generated by the control unit 203 or a signal generator 204 comprised by the control unit 203. Thus, if the control unit 203 does not have other functions than generating the input signal for the reflection unit, the control unit may be referred to as the signal generator 204.

The reflector unit 202 may be a mirror 206 which can be positioned in at least first and second positions where, in the first position, the projection direction 111 of the projector is unchanged and in the second position the image forming light from the projector 105 is redirected into the first direction 112. Thus, in the first mode of the reflector unit 202 the mirror 206 may be removed from the image forming light rays emitted by the projector 105 to let the light ray pass unobstructed. In the second mode the mirror 206 may be moved into the light rays to redirect the light ray into the first direction 112. The angle of the mirror 206 relative to the projection direction 111 and the first direction is determined according to Snell's reflection law.

Since the actual mode of the reflector unit 202 is dependent on the input signal received by the input 205, the surface 106, 107 where the image is projected onto can be controlled by the reflector unit 202 so that a patient in the scanner room is able to see the image whether the patient enters the room via the entrance 103 or is lying on the table 102. That is, the projection direction of the image forming light rays can be adjusted depending on the location of the patient.

Since the patient is normally lying with his back on the table and with the eyes directed towards the ceiling it is difficult to see an image projected onto a wall such as surface 112 shown in FIG. 1.

In order to enable the patient to conveniently view an image projected onto a wall a viewing device may be used to redirect the viewing direction from the patient's viewing direction towards the ceiling to a viewing direction towards one of the walls.

Figure 3:
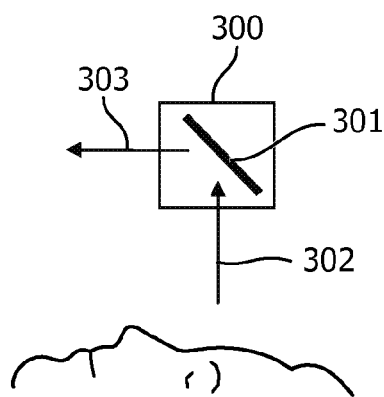
FIG. 3 shows a viewing device for redirecting the viewing direction of a patient.

FIG. 3 shows a viewing device 300 with one or two reflectors 301, e.g. one reflector for each eye, arranged to redirect the viewing direction of a patient from a vertical direction 302 to a horizontal direction 303. Thus, the viewing device enables the patient to see the projected image when the reflector unit is in the second mode.

The viewing device may be in the form of a pair of glasses to be worn by the patient or a mirroring device which is fixed to the table 102 or the scanner 101 so that it is located in front of the eyes of the patient.

The signal generator 204 in FIG. 2 may be a switch operable by the patient or clinical personnel. For example, when the patient is lying down on the table 102, the patient can change the mode of the mirror unit into the second mode so that the image from the image projector 105 is displayed on a surface which is visible to the patient. For example, in some scanners or in some scanner operations the ceiling may be visible to the patient and, therefore, the mirror unit may be operated to redirect the image to be displayed on the ceiling. However, often the scanner is constituted by a long narrow tunnel which surrounds the patient so that the only free viewing direction is along the tunnel, parallel with the floor. In this situation the image must be projected onto a wall surface adjacent one of the openings of the tunnel.

Instead of a manually operable switch, the signal generator 105 may be a detector capable of detecting when the patient is in a particular position required for performing a scanning operation. The detector 105 may be a contact switch or a pressure sensor arranged with the table so that when the patient is lying down a detector is activated by the patient's weight. The change of the detector is signaled to the input 205 of the mirror unit 202 for causing a mode change into the second mode. Alternatively, the signal generator may be a camera system configured with image analyzing capabilities for detecting the location or orientation of the patient or simply for detecting whether a person is located on the table 102. The signal generator 105 may also be a light ray detector arranged so that a passage of a light ray is obstructed when the patient is lying on the table 102.

In order to enhance the viewing experience by the user, 3D images may be projected onto the second room surface 107 instead of 2D when the reflector unit 105 is in the second mode. For that purpose, the image projector is switchable between projecting 2D images and 3D images so that 2D images are projected when the reflector unit is in the first mode and 3D images are projected when the reflector is in the second mode. Generation of 3D images where projection of 3D images comprise projection of relatively displaced first and second images which are coded, such as color or polarization coded, so that the first and second images are viewable by the respective left and right eye of the patient.

In this 3D embodiment, the image projector 105 may be comprised by the image projection system 201 and the image projector 105 may have an input 215 connectable with the signal generator 204 or the reflector unit 202 for receiving the input signal generated by the signal generator 204. The image projector may be configured to switch to 3D image projection when the input signal generated by the signal generator 204 for invoking a switch to the second mode of the reflector unit 205 is received by the input 215. Thus, when the patient enters the scanner room 100 a 2D image is projected on the adjacent wall 106 and when the patient lies down on the table 102, a 3D image is projected on the wall 107 which is visible for the patient.

In order to perceive the projected 3D images as 3D images, the viewing device 300 may comprise coded viewing elements, such as color or polarization coded mirrors or glass plates, for the respective left and right eye of the patient. Thus, if the slightly displaced first and second images of the projected 3D images are polarization coded or color coded correspondingly with the coding of the viewing elements for the left and right eyes so that the left eye viewing element only allows transmission of the first images and the right eye viewing element only allows transmission of the second images, the first and second images will be perceived as a 3D image, i.e. an image containing depth information. Such 3D imaging techniques also referred to as stereoscopy is described in various text books.

Figure 4:
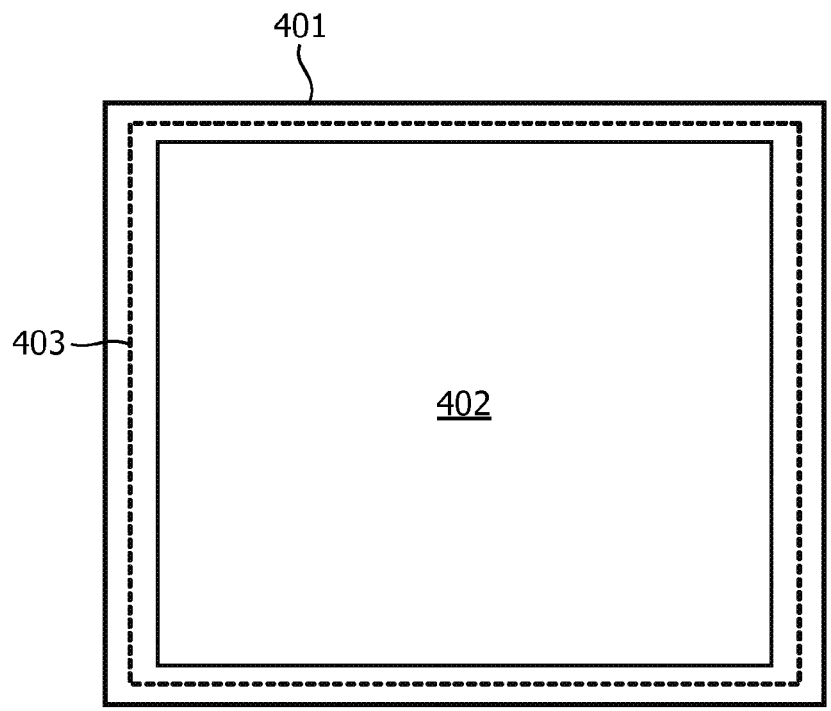
FIG. 4 illustrates the limited field of view of a patient.

FIG. 4 illustrates the outer boundary 401 field of view which is visible for the patient lying on the table of the scanner. The field of view may be limited due to the viewing device 300 or due to the tunnel shaped scanner which surrounds the patient. In order to enhance the viewing experience a border 403 can be created which at least partly encircles the image 402. The border may have a color and an intensity which matches the room lighting. In this way the patient experiences a more pleasant viewing of the image 402 since the border creates a gradual transition towards the outer boundary 401 of the field of view. Additionally, the border may include a zone wherein the image is gradually faded into the color of the room lighting, or the border 402 may contain other visual effects.

The image data which are responsible for creating the border may be created by a processor for pre-processing the image that is to be projected by the projector 105, for example by using the image data of the image 402 for creating a gradual washing out of the image 402. The border 403 may also be created in response to an auxiliary input (not shown) of the image projector containing data information about the color and intensity of the room lighting.

In order to further enhance the calming effect, the content of the projected images may be adapted to the patient's physiological conditions. For that purpose the image projection system may comprise a patient monitoring unit 298, e.g. a camera connected to an image processor, for detecting physiological parameters such as heart rate and breathing of the patient.

For example the heart rate can be determined from the camera image by analyzing images of the skin and breathing can be determined by comparing frames of the recorded images for determining motion frequency of the chest or the belly.

The adaption of the images to the measured physiological conditions can be performed by a processor comprised by the control unit 203 for generating or modifying the image signal supplied to the image projector 105 in dependence of the detected physiological parameters. For example, a different image theme may be selected in dependence of the detected physiological parameters.

In an embodiment the image projection system 201 comprises a surveillance system 299 with a camera, where the surveillance system has image processing capabilities—e.g. in the form algorithms processed by a processor for detecting faces—for detecting the presence of clinical personnel. If the presence of clinical personnel or any other person is detected, the surveillance system sends a signal to a processing unit comprised by the control unit 203, or to other data processing systems capable of for example:

switching on a spot light at a detected location of clinical personnel to ease work without disturbing the patient, lowering or muting a sound level of music when clinical personnel enters room and for achieving better patient communication, activating UV light if clinical personnel presents hands for disinfection, lowering the light level or shutter the image projector if staff is located in front of the projection surface, or muting or switching off the video when clinical personnel enters the scan room if they wish to limit their own exposure to annoying repetition of theme content.

As another example, when the system comprises a camera, the camera image may be processed for detection of an area of the image where clinical personnel is located, and using this area for blocking an area of the projected image where the personnel is present, e.g. by decreasing the intensity of the projected image in that area. Alternatively, a silhouette image of the clinical personnel may be created in the projected image. The blocking of a part of the projected image or creation of a silhouette may be performed by adjusting the intensity and/or color of light emitted by e.g. by the LCD screen of the image projector, e.g. by making all those pixels where the staff is 0 and the rest 1 and multiple with the content image to be projected.

Figure 5:
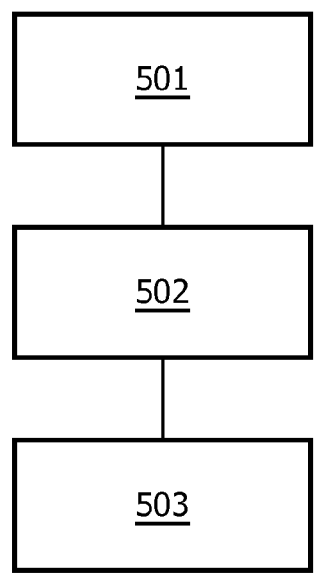
FIG. 5 shows methods steps according to an embodiment of the invention.

FIG. 5 illustrates method steps according to an embodiment of the invention, where:

step 501 comprises generating a signal indicating a location of a patient within the scanner room, step 502 comprises projecting an image from the image projector onto a first surface if the signal indicates a first location of the patient, and step 503 comprises projecting the image from the same image projector onto a second surface by redirecting the image using a reflector unit if the signal indicates a second location of the patient different from the first location.

Other or additional method steps according to further embodiments may be included.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality.

A single processor or other unit may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. An image projection system for use in a scanner room during a patient examination, comprising:

an image projector disposed in the scanner room for projecting images; a reflector disposed in the scanner room and configured to, in a first mode, project the images onto a first room surface and, in a second mode, project the images onto a second room surface, where the first and second room surfaces are non-coincident;

a controller configured to switch between the first and second modes based on patient location; and a surveillance system including a camera and configured to detect clinical personnel in the scanner room and in response to detecting clinical personnel, at least one of:

switching on a spot light at a detected location of clinical personnel, adjusting a sound level of music, activating a disinfector, lowering light level or shuttering the image projector, muting or switching off the image projector, blocking an area of or decreasing an intensity of the projected images at the location the clinical personnel is detected, and creating a silhouette image of the clinical personnel in the projected images.

2. The image projection system according to claim 1, further comprising a viewing device with one or two reflectors arranged to change the viewing path from a path between the patient and the first room surface to a path between the patient and the second room surface.

3. The image projection system according to claim 1, where the first surface is a surface adjacent to a patient entry of the scanner room and where the second surface is a surface visible to a patient lying on a table of a scanner of the scanner room.

4. The image projection system according to claim 1, further including;

a detector configured to detect when the patient is located in a scanning position.

5. The image projection system according to claim 1, where the image projector is configured to generate a border around the images.

6. The image projection system according to claim 1, where the reflector is further switchable into a third mode were the images are projected into a third surface which provides the patient entry to the scanner room.

7. The image projection system according to claim 1, comprising a patient monitor configured to detect physiological parameters of the patient, the controller being configured to generate or modify image information supplied to the image projector.

8. An image projection system for use in a scanner room for patient examination, where an image projector is installed in the scanner room for projecting an image onto a surface of the room, the image projection system comprising:

a reflector unit comprising a reflector, where the reflector is positioned relative to the image projector so that in a first mode of the reflector unit the miage is projected onto a first room surface, and in a second mode of the reflector unit the image is projected onto a second room surface, where the first and second room surfaces are non-coincident, and where a change from the first to the second mode is dependent on an input signal, a signal generator for generating the input signal indicative of a location of the patient, wherein the image projector is switchable between projecting 2D images and 3D images so that 2D images are projected when the reflector unit is in the first mode and 3D images are projected when the reflector is in the second mode, where projection of 3D images comprises projection of mutually displaced first and second images which are coded so that the first and second images are viewable by the respective left and right eye of the patient.

9. An image projection system for use in a scanner room for patient examination, where an image projector is installed in the scanner room for projecting an image onto a surface of the room, the image projection system comprising:
a reflector unit comprising a reflector, where the reflector is positioned relative, to the image projector so that in a first mode of the reflector unit the image is projected onto a first room surface, and in a second mode of the reflector unit the image is projected onto a second room surface, where the first and second room surfaces are non-coincident, and where a change from the first to the second mode is dependent on an input signal,
a signal generator for generating the input signal indicative of a location of the patient,
further comprising a viewing device with one or two reflectors arranged to change the viewing path from a path between the patient and the first room surface to a path between the patient and the second room surface, wherein the viewing devices comprises coded viewing elements for the respective left and right eye of the patient to enable viewing of the respective first and second images.

10. An image projection system for use in a scanner room for patient examination, where an image projector is installed in the scanner room for projecting an image onto a surface of the room, the image projection system comprising:
a reflector unit comprising a reflector, where the reflector is positioned relative to the image projector so that in a first mode of the reflector unit the image is projected onto a first room surface, and in a second mode of the reflector unit the image is projected onto a second room surface, where the first and second room surfaces are non-coincident, and where a change from the first to the second mode is dependent on an input signal,
a signal generator for generating the input signal indicative of a location of the patient, further comprising a surveillance system with a camera, where the surveillance system has image processing capabilities for detecting the presence of clinical personnel, and in dependence of a detected presence of clinical personnel changing a condition of the scanner room.

* * * * *